United States Patent [19]

McKenzie et al.

[11] Patent Number: 5,059,524

[45] Date of Patent: Oct. 22, 1991

[54] HLA-B27 TESTING

[75] Inventors: Ian F. C. McKenzie, Brunswick; Joe Trapani, Templestowe, both of Australia

[73] Assignee: The University of Melbourne, Victoria, Australia

[21] Appl. No.: 151,515

[22] PCT Filed: Feb. 26, 1987

[86] PCT No.: PCT/AU87/00055

§ 371 Date: Dec. 22, 1987

§ 102(e) Date: Dec. 22, 1987

[87] PCT Pub. No.: WO87/05398

PCT Pub. Date: Sep. 11, 1987

[30] Foreign Application Priority Data

Feb. 26, 1986 [AU] Australia ............... PH4811

[51] Int. Cl.⁵ ................ C07K 15/28; G01N 33/534; G01N 33/535; G01N 33/577

[52] U.S. Cl. ................ 435/7.24; 435/7.9; 435/188; 436/548; 436/811; 530/389; 530/391

[58] Field of Search ............ 435/7, 34, 188, 7.24, 435/7.9; 436/548, 811; 530/391, 389

[56] References Cited

PUBLICATIONS

G. D. Johnson et al., in D. M. Weir (Ed.), *Handbook of Experimental Immunology*–3rd Ed., Blackwell Scientific Publications, Oxford, UK, 1978, pp. 15.1–15.7.

Hood et al., *Immunology*, 2nd Edition, Benjamin/Cummings Publishing Co., Inc., Menlo Park, Calif., 1984, pp. 66–68.

Sternberger, *Immunocytochemistry*, Prentice Hall, Inc., Englewood Cliffs, N.J., 1974, pp. 50–53.

Larsen, *Transfusion* (Phila.), 19, 219–221, 1979.

Trapani et al., *Human Immunology*, 1, 205–216, 1983.

Trapani et al., *Immunol. Cell. Biol.*, 66, 215–219, 1988.

*Primary Examiner*—David Saunders
*Attorney, Agent, or Firm*—Scully, Scott, Murphy & Presser

[57] ABSTRACT

A method for testing for the HLA-B27 antigen which comprises mixing with blood cells or blood cell lysates a first antibody capable of binding and blocking the HLA-B7 antigen and a second antibody capable of binding to the HLA-B27 antigen wherein said second antibody is labelled so as to be detectable and thereafter detecting for the said labelled second antibody. The second antibody is specific to the HLA-B27 antigen. It is found that the HLA-B7 antigen binds in significant quantities to the second antibody. Therefore it is necessary to block the HLA-B7 antigen with said first antibody.

6 Claims, 5 Drawing Sheets

HLA-B27 TESTING

FIELD OF THE INVENTION

This invention relates to testing for the HLA-B27 antigen.

The disease ankylosing spondylitis (AS) is difficult to diagnose with certainty but it has been found that sufferers from AS have a probability of about 95% as being carriers of the gene coding for the HLA-B27 antigen.

The present invention provides a method of testing for the HLA-B27 antigen which comprises mixing with blood cells or blood cell lysates a first antibody capable of binding and blocking the HLA-B7 antigen and a second antibody capable of binding to the HLA-B27 antigen and wherein said second antibody is labelled so as to be detectable and thereafter detecting for the labelled said second antibody.

BACKGROUND OF THE INVENTION

Historically, only two methods for serological detection of HLA specificities have been popularly used since the introduction of routine tissue typing almost two decades ago. The first of these, a leukoagglutination technique, was replaced during the late 1960s by more sensitive and reliable cytotoxicity assays which were developed on a micro-scale by Kissmeyer-Nielson and by Terasaki, P. I. and McClelland, J. D.; Microdroplet assay for human serum cytotoxins, *Nature*, 206:998-1000 (1964). Microcytotoxicity remains standard today as it enables the simultaneous assessment of the reaction of a patient's cells with a very large number of scarce HLA typing sera which can be used in minute quantities.

Since the description of the close association of HLA-B27 with AS, a significant proportion of the labors of tissue-typing laboratories has been directed at assessment of HLA-B27 status, irrespective of the patient's full HLA phenotype. Requests for B27-typing by rheumatologists and other physicians have grown steadily despite frequent warnings that B27-status should rarely, if ever, be used as a diagnostic criterion for AS, as 8% of the (Caucasian) population is HLA-B27+ and only a small minority of these ever develop AS. At Royal Melbourne Hospital, for example, 45% of the 2500 requests for tissue typing during 1983 were solely for B27 status. Thus far, B27-typing has always been performed along routine tissue-typing lines, testing a panel of anti-B27 sera on the patient's lymphoctyes, and this has proven costly in terms of materials (especially antisera) and particularly because of recently escalating labor costs.

The aim of a full panel of standardized monoclonal HLA-typing sera is still a distant one, however, monoclonal antibodies may have much to offer in certain specific situations such as B27-typing. Accordingly, a number of procedures which have utilized an anti-HLA-B27 monoclonal antibody, have been developed, which should enable rapid, cheap and dependable assessment of B27 status. It is contended that these techniques will lead to a marked reduction in the costs of HLA-B27 typing, both in terms of staff labour and the costs of disposable reagents, allowing the direction of these resources to other services.

SUMMARY OF THE INVENTION

A method of testing for the HLA-B27 antigen which comprises mixing with blood cells or blood cell lysates a first antibody capable of binding and blocking the HLA-B7 antigen and a second antibody capable of binding to the HLA-B27 antigen wherein said second antibody is labelled so as to be detectable and thereafter detecting for the said labelled second antibody. The second antibody is specific to the HLA-B27 antigen. The HLA-B7 antigen binds in significant quantities to the second antibody. Therefore, it is necessary to block the HLA-B7 antigen with said first antibody.

DESCRIPTION OF THE PREFERRED EMBODIMENTS

Figure 1:
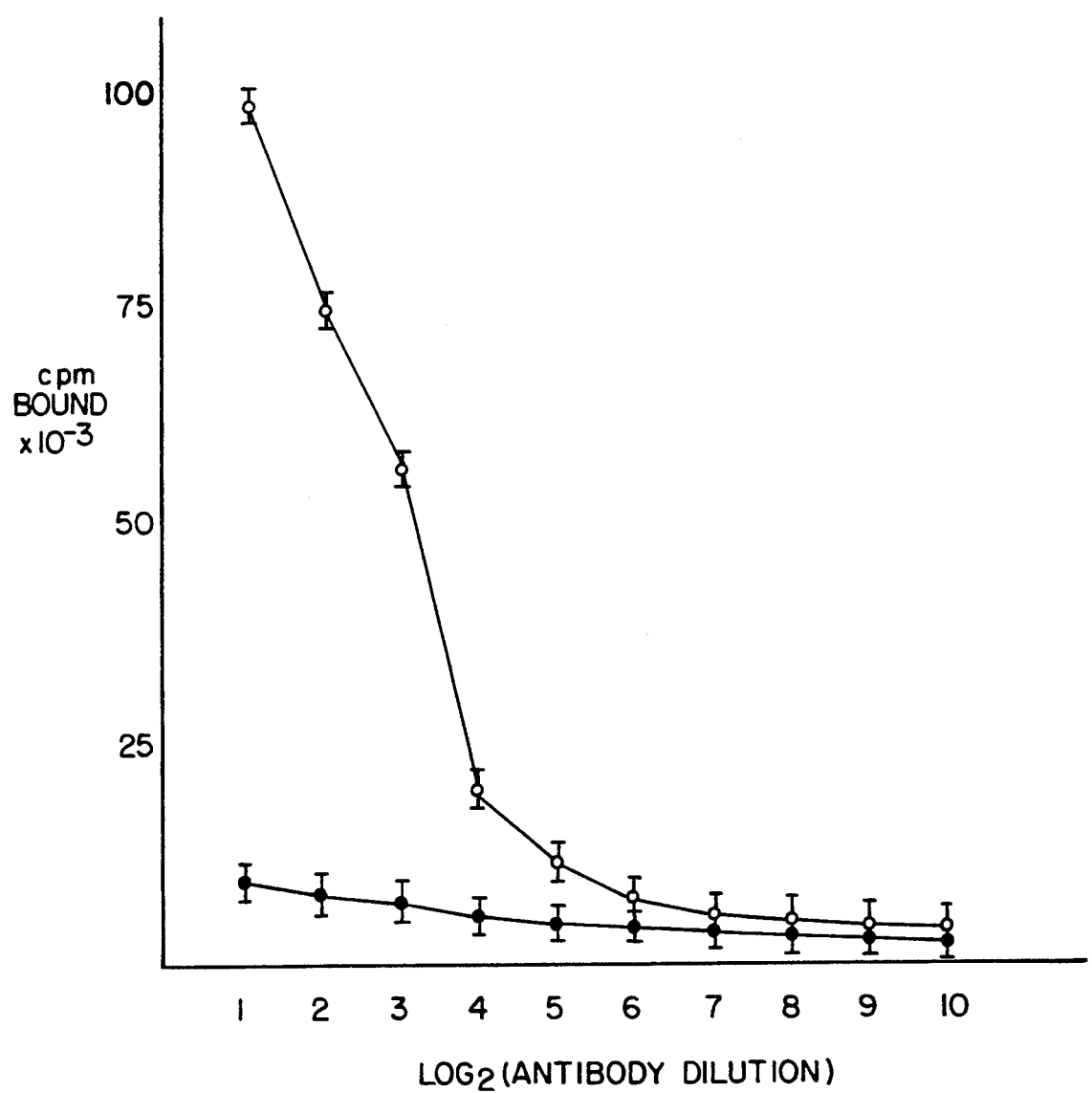
FIG. 1: A titration of $^{125}$I-labelled anti-HLA-B27 monoclonal antibody on cell lysates of HLA-B27+ and B27− peripheral blood lymphocytes. Points on each curve represent the mean of triplicate assays ± standard error (cpm=counts per minute).

In a preferred aspect there is provided a method of testing for the HLA-B27 antigen which comprises forming a mixture containing blood cells or blood cell lysates, a first antibody capable of binding and blocking the HLA-B7 antigen and a second antibody capable of binding to the HLA-B27 antigen, wherein the second antibody is labelled to be detectable and thereafter separating unbound said second antibody from the mixture and detecting for said second antibody bound to HLA-B27 antigen.

In a preferred aspect the present invention provides a composition for testing for the HLA-B27 antigen comprising a mixture containing a first antibody capable of binding and blocking the HLA-B7 antigen and a second antibody capable of binding to the HLA-B27 antigen and wherein said second antibody is labelled so as to be detectable.

The blood used in the method of testing may be whole blood, citrated blood or blood depleted of erythocytes. Various diluents may be added to the blood. In general, it is preferred that the methods of this invention be performed on whole blood as so doing reduces testing time and cost.

Said first antibody may be any suitable antibody and no particular antibody is required. However, we currently prefer to use as said first antibody a HLA-B7 specific antibody designated BB7.1 produced by a cell line obtained from Dr. Peter Parham of the Imperial Cancer Research Foundation, London, England.

Said second antibody may be any suitable antibody and no particular antibody is required. However, we currently prefer to use as said second antibody HLA-ABC-m3 which is a HLA-B27 specific antibody produced by the Department of Pathology, University of Melbourne, Melbourne, Victoria, Australia.

Said second antibody may be labelled to be detectable in any convenient way. It is currently preferred to use radio-labelling but colorimetric and enzyme-linked immunosorbent assay (ELISA) labelling may also be applied.

In one preferred manner of labelling, said second antibody was labelled with $^{125}$I. Such labelling may be done in any suitable manner. In one preferred instance purified monoclonal antibody is mixed with $^{125}$I (radioactive iodine) and chloramine T is added; after 1-2 mins at room temperature, sodium metabisulphite is added to neutralise the chloramine T and the $^{125}$I-antibody is separated from free $^{125}$I using exclusion chromatography. The $^{125}$I is bound covalently to tyrosins residues in the antibody.

In a colorimetric labelling, said second antibody was labelled with a dye such as Procion Blue MX-R obtained from Fluka AG, Switzerland or ICI Limited, England.

In an ELISA labelling said second antibody was labelled with an enzyme and later reacted with a suitable substrate adapted to change colour on such a reaction occurring. Enzymes and substrates therefor considered suitable include gelactosidese and 2-nitrophenyl-B-D-galactopyranoside; peroxidase and 3,3-diaminobenzidine, peroxidase and ABTS, and urease and phenyl red, (ABTS is 2,2'-azino-di(3-ethyl) benzothiazoline sulphonate).

Separation of unbound said antibody from the mixture may be effected in any convenient way but in general centrifugation is satisfactory and produces a cell pellet and a supernant which can be decanted. The cell pellet can be washed as necessary.

EXAMPLES

A. Standard Procedures

Cell lines: Three lymphoblastoid cell lines were used
(i) Bordin: HLA type A2, A2; B27, Bw39; DR1
(ii) LD-B: homozygous typing cell, HLA type A3;B7;DR2
(iii) JZ-B: HLA type Aw23,A32; Bw21, B16; DR4,5
Cells were grown in RPMI medium.

Monoclonal Antibodies: HLA-ABC-m3, which detects an HLA-B27-specific determinant. HLA-ABC-m1 detects an HLA-Class 1 "framework" antigen while BB7.1 is an HLA-B7-specific monoclonal antibody.

Leukocyte/Platelet Preparations: A suspension of leukocytes and platelets was prepared by mixing 5 ml of citrated blood with 1 ml of 6% w/v dextran (Pharmacia) in 0.9% NaCl in an elongated tube. After mixing, the tube was allowed to stand at RT for 30 min, permitting agglutinated red cells to settle. The supernatan leukocytes and platelets were collected and stored in a separate tube at ambient temperature until used.

Cell Lysates: Tissue culture cells were washed once in 0.9% NaCl then lysed at $10^8$/ml in a solution of 0.5% (v/v) Triton X-100 (BDH) and 10 mM Iris-HCl,pH 7.4 in physiological saline (TTS) which was supplemented with 1% (w/v) (bovine serum albumin)(BSA) and 1% (v/v) trasylol. The mixture was incubated on ice for 60 min. then cell nuclei and debris were removed by centrifugation. The supernatant membrane preparation was either used immediately or stored frozen at $-80°$ C. til used.

Purification of HLA-ABC-m3 by protein A (pA) Affinity Chromatography: To remove lipid material from ascites prior to purification, an equal volume of Freon ($ClCF_2CCl_2F$; Aldrich Chemical Company, Inc., Milwaukee, Wis., USA) was added, mixed well, and the suspension was centrifuged. The recovered ascites was added dropwise to a pA-Sepharose column prewashed with phosphate buffered saline (PBS). After further washing with PBS, antibody was eluted with glycine-HCl, pH 2.8 (Sigma Chemical Co.). To neutralise the pH of the eluate, 1 ml fractions were collected in tubes containing 5 microl of saturated tris buffer. The absorbance of each fraction was determined and tubes containing the eluted protein retained. The column was washed with glycine-HCl, pH 2.8 until all protein was removed. The pooled protein sample of known concentration was dialysed against bicarbonate buffer (0.1M $NaHCO_3$, 0.5M NaCl, pH 7.5) at 4° C. overnight.

Radioiodination: HLA-B27 monoclonal antibody was radiolabelled with $^{125}$I (Amersham International) as described above.

B. Experimental Protocols

Three different assays are presented here, the first detecting B27 antigen in membrane preparations, the second and third on intact cells. The first two methods are described briefly as the third is clearly the method of choice for HLA-B27 typing and therefore has been refined to the greatest degree.

1. A Radioimmunoassay for Detection of Detergent Solubilised. Cell-Membrane Bound HLA-B27: This method was devised to detect HLA antigens in membrane preparations of cultured cell lines. In this two step "sandwich" procedure, a first monoclonal antibody that detects a monomorphic HLA class 1 determinant was bound onto a PVC plate which had previously been coated with pA. Membrane-bound HLA antigents were than allowed to bind to this antibody and HLA-B27 was detected by the addition of $^{125}$I-labelled HLA-ABC-m3. The assay was performed at room temperature (RT) in a moisture box and in triplicate.

Protocol 1:

(1) A flexible PVC plate (Disposable Products) was coated with pA (50 microl of a 50 micro g/ml solution) (Sigma Chemical Co.).

(2) Non-specific protein-binding sites were blocked by topping up the wells with 1% solution of BSA in PBS for 30 min.

(3) The plate was "flicked" and washed three times with PBS then HLA-ABC-m1 (50 microl of a 1/100 dilution of mouse ascitic fluid) was added to each well for 60 min.

(4) The plate was rewashed as above and cell lysate added (50 microl doubling dilutions) for four hours.

(5) Following further washing, radiolabelled HLA-ABC-m3 ($5 \times 10^5$ cpm of antibody at a specific activity of approx. 1.8 micro Ci/micro g protein diluted in PBS with 1% BSA) was added and incubated overnight.

(6) On the next day, the plate was washed, dried and the bound radioactivity estimated.

Results: This method was able to discriminate between B27+ and B27− cell lysates consistently and accurately, with lysate dilutions as low as 1/16 (FIG. 1) and similar results were obtained whether cell lines or leukocyte preparations were used as an antigen source. However, there were several disadvantages in this procedure. For example, the protocol had several long incubations, the total assay taking about twenty hours. Furthermore, there was the necessity of separating the patient's leukocytes and then processing these to produce a membrane preparation. Attempts were made to adapt the assay to detection of HLA antigens in serum or urine, but this protocol lacked the sensitivity required to detect such small quantities of antigen (not shown).

2. A Direct-Binding Radioimmunoassay for Detection of HLA-B27 in Leukocyte-Platelet Preparations: This method for detection of HLA-B27 consisted of a direct binding assay of radiolabelled anti-B27 monoclonal antibody performed on citrated blood, depleted of erythrocytes by dextran sedimentation. The advantages of this method were that the antigen source (i.e. the crude, unwashed preparation of leukocytes and platelets) was easy to prepare and the protocol was shorter compared with the previous method. This protocol was also performed at RT and in triplicate.

Protocol 2:

(1) Doubling dilutions of $^{125}$I-labelled HLA-B27 antibody (50 microl, commencing with $2 \times 10^6$ cpm/assay) were set up in 3 ml disposable plastic test-tubes (Disposable Products) which had previously been treated with PBS containing 1% BSA in order to prevent non-specific protein binding.

(2) Leukocytes and platelets were isolated from whole blood as described above and 500 microl of the suspension added to each tube for 30 min.

(3) The cells were washed twice in PBS/BSA and bound radioactivity estimated.

Figure 2:
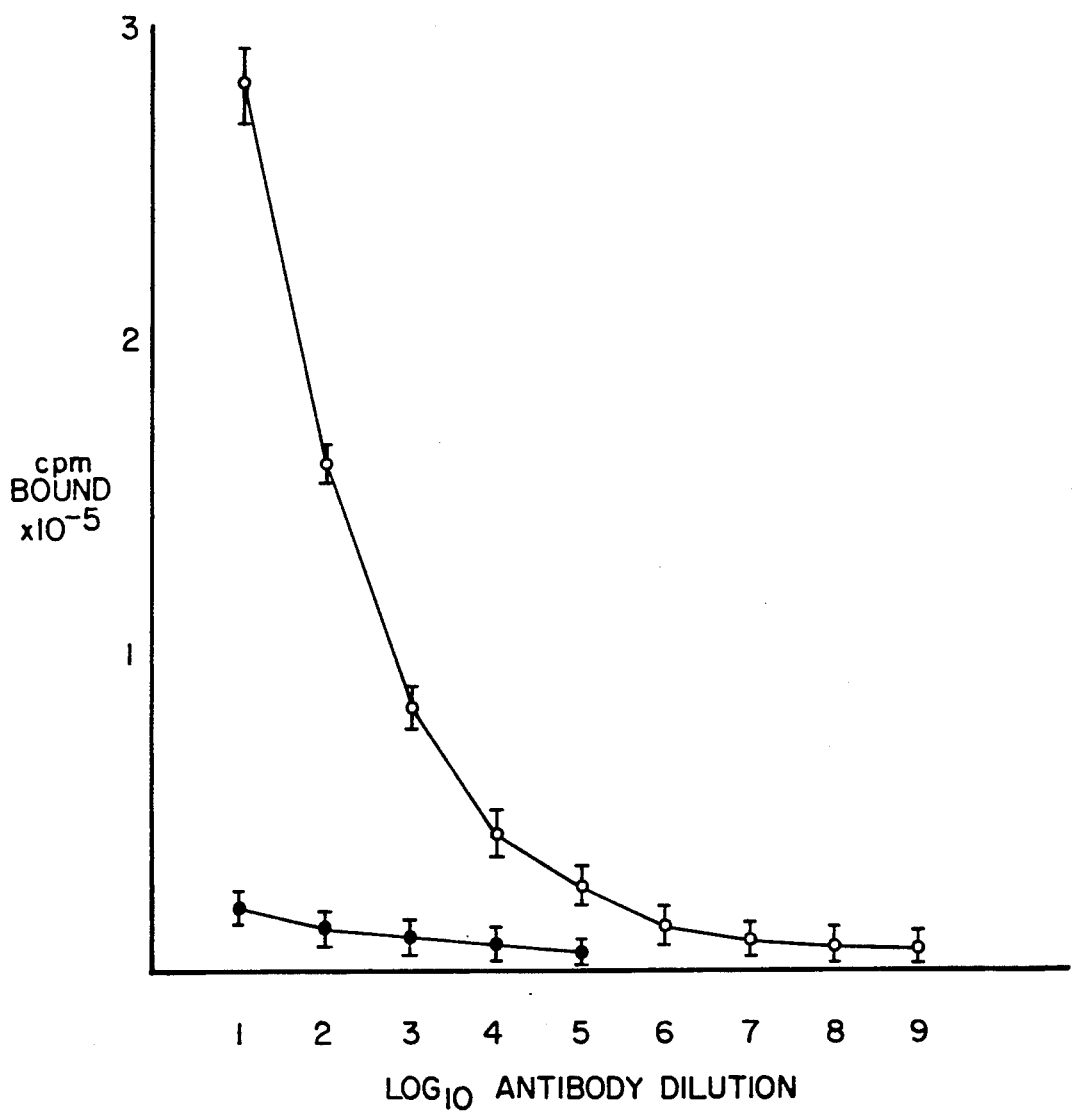
FIG. 2: A titration of $^{125}$I-labelled anti-HLA-B27 monoclonal antibody on leukocyte/platelet suspensions derived from HLA-B27+ and B27− subjects. Points on each curve represent the mean of triplicate assays ± standard error.

Results: This method proved most satisfactory, with specific/non-specific binding ratios of up to 100:1 (FIG. 2). The assay was simple, rapid and reliable, with the possibility of analysing up to six or eight samples within two hours. Attempts were made to adapt this procedure to an assay in a flexible PVC plate, however difficulties were experienced with the washing procedures. In developing a direct binding assay it was anticipated that false positives might be encountered when testing the leukocytes of individuals bearing determinants which are cross-reactive with HLA-B27. It had already been shown in two large population studies that apart from HLA-B27+ cells, only HLA-B7+ cells were able to bind significant quantities of HLA-ABC-m3, the affinity of the antibody for this specificity being approximately one log unit less than that for HLA-B27. It was thus reasonable to presume that HLA-B7 would cause the greatest problems with false positive assignment of B27-status. HLA-B7 is a commonly encountered HLA specificity in Caucasian populations, to the extent that approximately 4% of such populations are HLA-B7 homozygotes. Binding assays using radiolabelled anti-HLA-B27 and a number of cell lines confirmed this suspicion. It was shown that a 87 homozygous cell line, LD-B bound almost as much HLA-B27 as did the B27 heterozygous cell line, Bordin (Table 1) and that this binding persisted despite several washes. The same phenomenon was noted when leukocytes were used instead of cell lines. Attempts to reduce this "background" binding are described below.

3. A Direct-Binding Radioimmunoassay for Detection of HLA-B27 in Whole Blood: The direct binding assay described below was analagous to that described above, however it had the advantage of using whole blood rather than a leukocyte preparation, thus rendering the protocol extremely simple. Once again, it was performed at RT and in triplicate.

TABLE 1

| | Binding of Radioiodinated HLA-ABC-m3 to HLA-B27+ and HLA-B27− Cell Lines* | |
|---|---|---|
| Cell Type | HLA Phenotype | Cpm Bound |
| Boroin | A2,A2;B27,Bw39;DR1,DR1 | 467,980 ± 12,000 |
| LD-B | A3,A3;B7,B7;DR2,DR2 | 417,300 ± 32,000 |
| JZ-B | Aw22,Aw32;B16,Bw21;DR4,DR5 | 700 ± 500 |

*Figures expressed are the mean of triplicate assays ± standard error.

Protocol 3:

(1) Radiolabelled anti-HLA-B27 antibody (approximately $4 \times 10^5$ cpm) was placed in a plastic test-tube which had been pretreated with PBS containing 1% BSA in order to prevent non-specific protein binding.

(2) Whole blood (250 microl) was added to each tube for 30 min with gentle agitation every 10 minutes.

(3) The tubes were centrifuged and supernatant was removed from the cell pellet products.

(4) The cell pellet was washed twice in PBS/BSA and bound radioactivity estimated.

Figure 3:
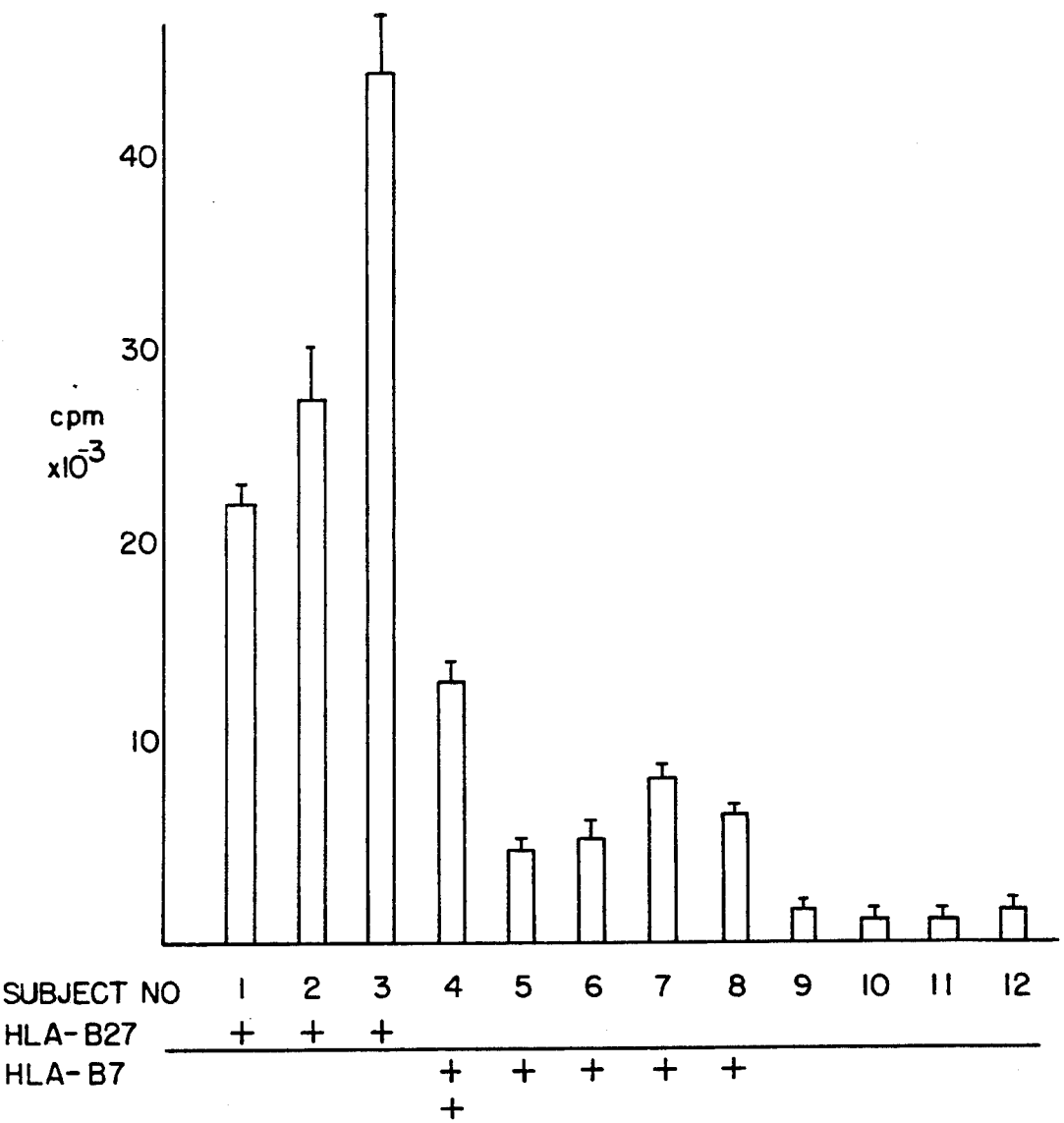
FIG. 3: Direct binding assay of $^{125}$I-labelled anti-HLA-B27 monoclonal antibody on whole blood derived from a panel of 12 subjects who were either HLA-B27+ (subjects 1-3), HLA-B7+ (subjects 4-8) or who lacked specificities (subjects 9-12). Subject 4 was homozygous for HLA-B7. Radioactivity bound represents the mean of triplicate assay +standard error.

Results: Protocol 3 was used to examine 12 subjects for B27 status (FIG. 3). The study population was chosen to include individuals who were heterozygous for HLA-B27, heterozygous or homozygous for HLA-B7 or who possessed neither of these specificities. The B27+ individuals were able to bind between 22,000 and 44,000 cpm, while the only B7 homozygote available for study bound approximately 13,000 cpm. By comparison B7 heterozygotes were in the range 4,000-8,000 cpm, with B27−B7− individuals binding far less antibody (600-800 cpm).

Although these results were encouraging, they also confirmed the likelihood that B7 homozygous individuals could be confused with B27 heterozygotes. Accordingly, it was decided to attempt to block the non-specific binding of the anti-HLA-B27 antibody by preincubating the cells with a second monoclonal antibody (BB7.1) which specifically detects an epitope on the HLA-B7 molecule but fails to react with HLA-B27. Importantly, previous population studies have shown that the epitope defined by BB7.1 is present on the cells of 100% of individuals who are typed as HLA-B7+ by conventional means.

Figure 4:
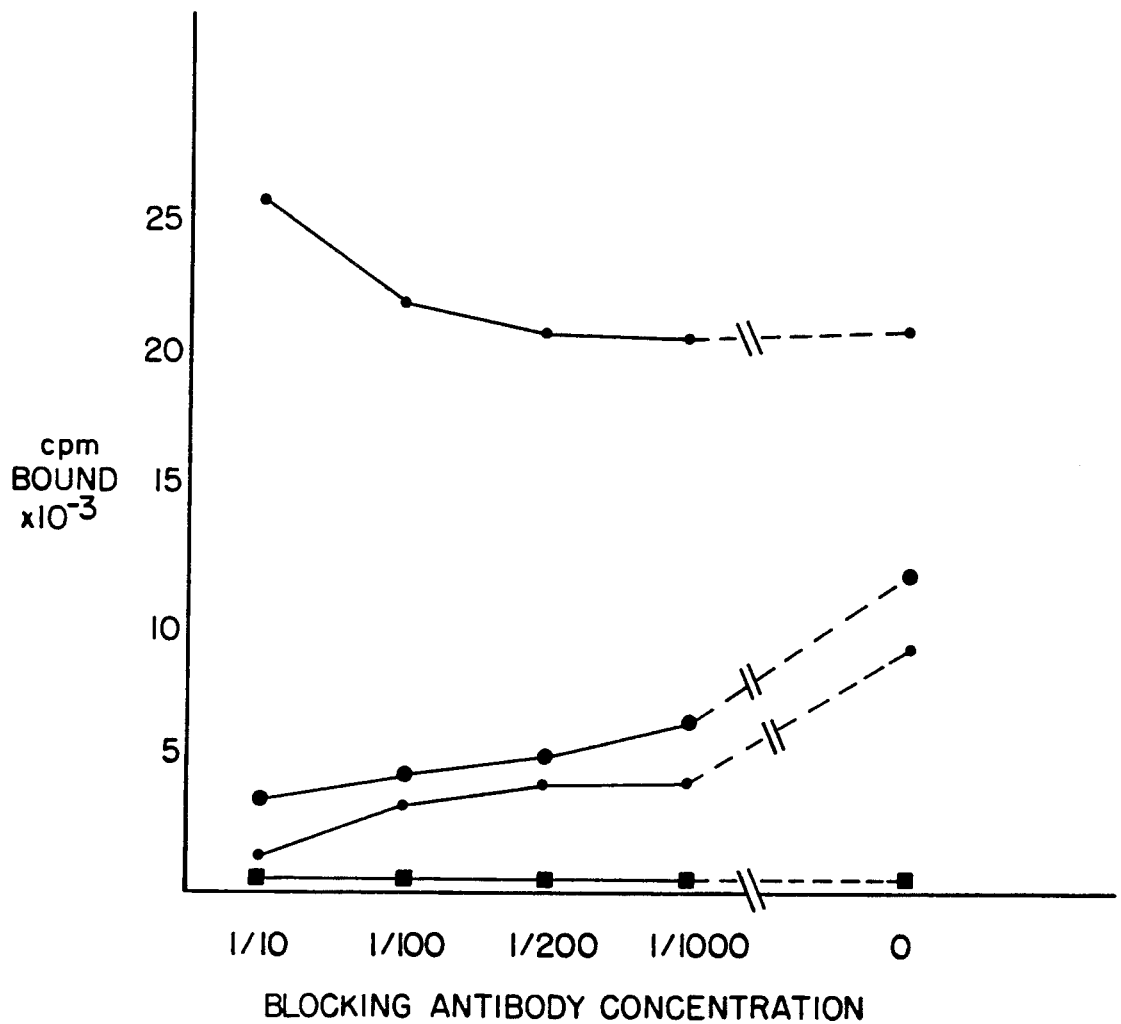
FIG. 4: Inhibition of the binding of $^{125}$I-labelled anti-HLA-B27 monoclonal antibody, to the whole blood of HLA-B27 heterozygous, HLA-B7 homozygous, and HLA-B7 heterozygous individuals and to the whole blood of individuals lacking both of these specificities following preincubation with various concentrations of anti-HLA-B7 monoclonal antibody BB7.1. Binding levels with no inhibition by BB7.1 are shown at right.

Protocol 3 was thus modified to include a step in which the blood sample was preincubated for 20 minutes with various dilutions of BB7.1 prior to addition of the radiolabelled anti-HLA-B27 antiserum. In order to keep the protocol as brief as possible, no washing took place until after incubation with anti-HLA-B27. The cells of four individuals were studied (Subjects 1, 4, 7 and 10 in FIG. 3) as they represented the four study populations, i.e. B27 heterozygotes, B7 homozygotes, B7 heterozygotes and B27−B7− individuals (FIG. 4). At the highest concentrations of blocking antibody, "non-specific" binding of the anti-B27 reagent was reduced by 72% in the case of the B7 homozygote and by 85% in the case of the B7 heterozygote, while there was no reduction in the ability of anti-HLA-B27 to bind to B27+ cells.

Figure 5:
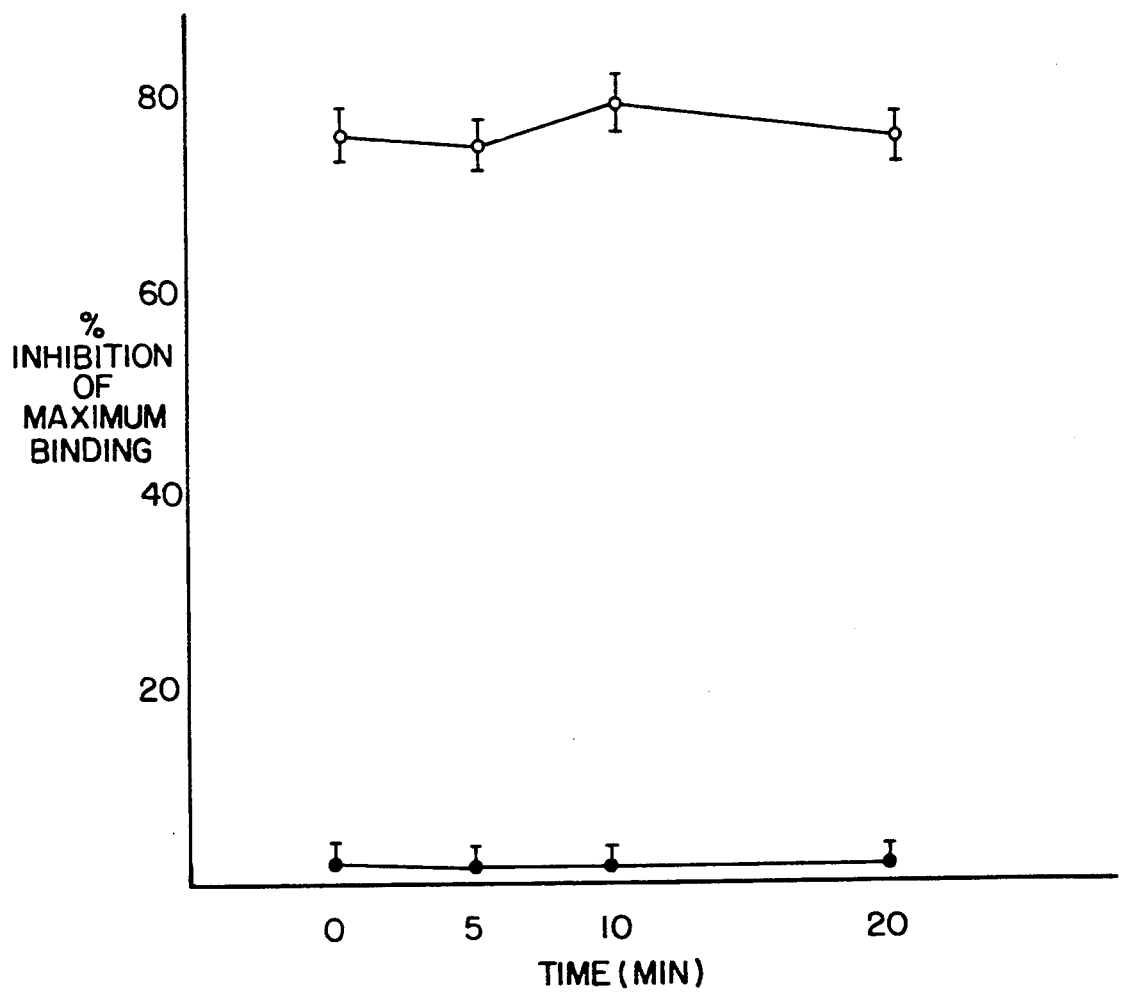
FIG. 5: Percentage inhibition of the binding of $^{125}$I-labelled anti-HLA-B27 monoclonal antibody to whole blood from HLA-B7 homozygous and HLA-B27 heterozygous individuals, following pre-incubation for varying lengths of time with anti-HLA-B7 monoclonal antibody (BB7.1). Where time=0, the blocking antibody was added immediately after the radiolabelled antiserum. Points on each curve represent the mean of triplicate assays ± standard error.

Subsequently, it was shown that simultaneous addition of blocking antibody and test antibody produced the identical degree of blocking of HLA-B7+ cells as that produced when the anti-B7 reagent preceded the radiolabelled anti-B27 antibody. This was demonstrated in a time course experiment (FIG. 5) in which the anti-B7 reagent was preincubated with B7 homozygous and B27 heterozygous blood samples for varying lengths of time prior to the addition of the B27-specific reagent. Clearly, the degree of blocking was not affected by the length of preincubation with anti-HLA-B27. This was a significant finding as it permitted further abbreviation of the protocol.

The favoured protocol was therefore as follows:

(1) Test-tubes can be prepared and stored as follows: test-tubes are filled with PBS/BSA and incubated at RT for 30 min then emptied by flicking. Radiolabelled anti-HLA-B27 antibody (50 microl, radioactivity of $4 \times 10^5$ cpm) and blocking antibody (20 microl of BB7.1 ascites fluid prediluted 1/10 with PBS/BSA) are then added, the tubes are tightly capped and stored at 4° C. If $NaN_3$ is added to a final concentration of 0.1% (w/v), the tubes can be stored for at least one week.

(2) Blood to be tested (250 microl in triplicate assays) is added to each tube and incubated at RT for 30 min.

(3) The cells are then washed twice with PBS/BSA, test tubes were centrifuged and the settled cell pellet drained of all fluid and bound radioactivity is estimated in gamma counter.

In order to test the final protocol, a series of blood samples which were submitted to the Royal Melbourne Hospital for B27 typing were tested in parallel with conventional microcytotoxicity, which was performed independently. A total of 19 blood samples were tested and it was found that the B27+ individuals detected by each technique correlated exactly (Table 2). All four HLA-B27+ individuals were able to bind at least ten times as much radioactivity as the B7+ subjects, enabling easy differentiation of HLA-B27+ from cross-reactive specificities.

TABLE 2

| HLA-B27 Status Determined by RIA and by Microcytotoxicity | | | |
|---|---|---|---|
| Subject | HLA-B27* | HLA-B7* | cpm bound $\times 10^{-3}$(a) |
| Experiment 1 | | | |
| 1 | − | − | 2.0 ± 0.2 |
| 2 | − | − | 1.2 ± 0.2 |
| 3 | + | − | 21.2 ± 2.5 |
| 4 | − | − | 1.9 ± 0.3 |
| 5 | + | − | 27.6 ± 2.1 |
| 6 | + | − | 55.4 ± 2.2 |
| 7 | − | − | 0.8 ± 0.4 |
| 8 | − | − | 1.3 ± 0.2 |
| 9 | + | − | 33.3 ± 3.0 |
| 10 | − | − | 1.7 ± 0.2 |
| 11 | − | + | 2.0 ± 0.4 |
| 12 | − | + | 2.7 ± 0.2 |
| (13) | HLA-B27+ | control subject | 33.4 ± 2.1 |
| Experiment 2 | | | |
| 1 | − | + | 1.4 ± 0.2 |
| 2 | − | − | 1.4 ± 0.2 |
| 3 | − | − | 0.9 ± 0.2 |
| 4 | − | + | 1.8 ± 0.3 |
| 5 | − | − | 0.8 ± 0.1 |
| 6 | − | − | 0.8 ± 0.4 |
| 7 | − | − | 0.9 ± 0.3 |
| (8) | HLA-B27+ | control subject | 25.4 ± 1.3 |

*as determined by standard microcytotoxicity at Royal Melbourne Hospital Tissue Typing Laboratory
(a) mean of triplicate assays ± standard error Next, 142 patients typed by the conventional cytotoxicity test in another laboratory (Dr. B. Tait, Tissue Typing Laboratory, Royal Melbourne Hospital) and by the radio-immuno-assay RIA in our laboratory.

106/142 were HLA-B27− by both cytotoxicity and RIA

36/142 were HLA-B27+ by both cytotoxicity and RIA

25/142 were HLA-B7+ by cytotoxicity and were negative by RIA.

Note: Two patients deserve comment

No. 1: Cytotoxicity was weak but RIA−

No. 2: Initially called B27+ by cytotoxicity but was RIA−.

On repeat of both tests the result was cytotox−, RIA−, i.e. the RIA was the better used, i.e. no discrepancies in 142 tests.

ELISA ASSAY FOR THE DETECTION OF THE HLA-B27 ANTIGEN

Introduction

The Elisa test is now taking the place of radioimmunoassays (RIA) in a number of laboratories for the following reasons: (i) to avoid the handling of radioactive isotopes, (ii) to use reagents which do not decay with time (such as radioactivity) and have a long shelf life. The principle of Elisa in this case is the same as outlined from the RIA—an enzyme, (for example beta-galactosidase but many others can be used), is linked to the antibody and the amount of antibody bound to the antigen is measured by finding the amount of enzyme bound. The enzyme is detected by adding a substrate which changes colour (measured by optical density). Thus the measurement of enzyme bound measures the amount of HLA-B27 antigen which is present.

Preparation of anti-HLA-B27 antibody-beta-galactosidase enzyme Conjugate

1. Beta-galactosidase was coupled to anti-B27 antibody using the crosslinker succinimidyl 4-(N maleimidocyclohexane carboxylate) (SMCC). Briefly antibody (1 ml, 2.25 mg/ml) was treated with a 6 fold excess of SMCC and after a period of 30 mins dialysed overnight into phosphate buffer, pH 7.5, 0.01M, 0.15M NaCl. The modified antibody was then reacted with beta-galactosidase (1.5 fold excess) and after a period of 30 mins applied to a column of Sepharose 6B (1.5 cm × 100 cm) equilibrated in phosphate buffer. The high molecular weight fraction containing enzyme activity was pooled and stored at 4° C. with 1% BSA (bovine serum albumin).

2. Target. Whole blood or cells were taken from three individuals:

1. K.V. B27 +ve, B7 −ve. 2. M.S. B27 −ve, B7 +ve. 3. G.T. B27 −ve, B7 −ve.

3. Substrate. 2-nitrophenyl-beta-D-galactopyranoside (Boehringer). Make up to 0.67 mgs/ml in a phosphate buffer and sonicate to dissolve (0.1M Phosphate, pH 7.5, 3.3 mM $NgCl_2$, 0.1M 2 me).

4. Plates. Round bottomed, rigid 96 well, blocked with 3% BSA/PBS for 1 hour at room temperature.

5. Assay.
   a. Doubling dilutions of B27-enzyme conjugate (1:1 for 24 wells in duplicate); 25 microl/well with dilutions in the phosphate buffer.
   b. Added 25 microl of anti-HLA-B7, dilution 1.25 with a final dilution of 1:50.
   c. Added 50 microl of whole blood per well and mixed,
   d. Incubated on ice for 30 minutes.
   e. Washed with PBS ($\times 4$).
   f. Add 100 microl of substrate, vortex and incubate at room temperature for 30°.
   g. Stop reaction with 25 microl of 1.6M $Na_2 CO_3$.
   h. Controls — +ve 25 microl B27 conjugate + 100 ml substrate; —ve 25 microl phosphate buffer + 100 ml substrate.
   i. Plates were spun and examined colour of the supernatant—this was done by measuring the optical density but could be scored by eye. In this way the maximum score (4) was achieved by the known positive (+) and zero (—) by the known negative (—) control; the colour in the tests could therefore be accorded zero to 4.

Results (See Table 3)

The Control (+) read 4 whereas the negative control read (—). The three individuals varied in their reaction. If 2 was taken as the cut-off then the tumour positive (KV) recorded a titre of 1:8, a B7 individual (MS) of 1:1 and negative (GT) of 1:2. Thus the positive and negative reactions could be clearly distinguished by the Elisa method of testing.

TABLE 3

| | Dilution of Antibody | | | | | | | | | | | |
|---|---|---|---|---|---|---|---|---|---|---|---|---|
| | 1 | 2 | 4 | 8 | 16 | 32 | 64 | 128 | 256 | 500 | 1000 | 2000 |
| Individual | 1 | 2 | 3 | 4 | 5 | 6 | 7 | 8 | 9 | 10 | 11 | 12 |
| KV | 3 | 3 | 2 | 2 | 1 | 1 | — | — | — | — | — | — |
| Duplicate Well | 3 | 3 | 2 | 2 | 1 | 1 | — | — | Titre = 1:8 | | | |
| | — | — | — | — | — | — | — | — | — | — | — | — |
| MS | 3 | 1 | 1 | — | — | — | — | — | Titre = 1:1 | | | |
| Duplicate Well | 3 | 1 | 1 | — | — | — | — | — | — | — | — | — |
| | — | — | — | — | — | — | — | — | — | — | — | — |
| GT | 3 | 2 | 1 | 1 | — | — | — | — | Titre = 1:2 | | | |
| Duplicate Well | 3 | 2 | 1 | 1 | — | — | — | — | — | — | — | — |
| | — | — | — | — | — | — | — | — | — | — | — | — |
| Controls | | | | | | | | | | | | |
| +ve | 4 | 4 | 4 | 4 | | | | | | | | |
| —ve | — | — | — | — | | | | | | | | |

It must be stressed that the results presented have examined only a very small study population and have served only to standardise the procedure. Given that such parameters as peripheral white cell count, platelet count, haematocrit and the level of expression of Class 1 antigens vary substantially within a normal population, it is feasible that occasional errors may occur. For example, an HLA-B7 homozygote with a leukocytosis might bind nearly as much radioactivity as a B27 heterozygote with a mild leukopenia or thrombocytopenia. It is likely that the false positive rate will be very low as the only group likely to produce such a result is the B7 homozygous population and these account for only 3–4% of Caucasions, while false negatives should be rare, according to population studies which showed that 100% of B27+ individuals were detectable with HLA-ABC-m3.

It is also of interest that binding of BB7.1 to HLA-B7+ cells was able to mask a determinant on the B7 molecule which cross-reacts with an anti-HLA-B27 monoclonal antibody. This suggests that the two epitopes involved may be epatially close to one another, resulting in steric hindrance when the two antibodies compete for binding sites or possibly, that binding of the anti-B7 antibody causes conformational changes in the B7 molecule, such that the avidity of the interaction between the anti-B27 antiserum and its target is substantially reduced. A disadvantage of one aspect of the proposed B27-typing technique is that it involves the use of radioisotopes. However, it should be noted that current protocol uses small amounts of a relative innocuous isotope and minimal handling of the reagent is required. Radioiodinated HLA-B27 retains its activity for up to four weeks if stored at 4° C., and each iodination of 100 microg of purified antibody provides sufficient reagent for 2,000 tests. It would thus be necessary only to dilute the antibody once per week and to aliquot it into the requisite number of tubes, ready for the addition of blood. The iodination procedure per se would then need to be carried out only once per month. The alternative aspects of colourimetric assay and ELISA do not suffer this defect.

DISCUSSION

This specification describes alternative methods of ascertaining B27 status, which has several advantages over conventional microcytotoxicity. The assays are rapid, accurate, reproducible and are capable of reliably differentiating HLA-B27, from serologically cross-reactive specificities, especially HLA-B7, by use of a blocking step to "mask" cross-reactive determinants on the B7 molecule. Given the large number of requests for B27-typing and the "labour intensive" nature of the method presently used, it may now be possible to significantly reduce the cost of providing a B27-typing service while simultaneously preserving valuable tissue typing reagents.

We claim:

1. A method of testing for the HLA-B27 antigen in blood cells and blood cell lysates which comprises forming a mixture containing said blood cells or said blood cell lysates, a first antibody which binds and blocks the HLA-B7 antigen and a second antibody which binds the HLA-B27 antigen, wherein the second antibody is labelled; and thereafter separating the unbound second antibody from the mixture and detecting said labelled second antibody bound to said HLA-B27 antigen and thereby detecting the presence of HLA-B27 antigen.

2. A method as claimed in claim 1, wherein said second antibody is radio-labelled.

3. A method as claimed in claim 1, wherein said second antibody is labelled with an enzyme to react with a substrate to produce a detectable change.

4. A composition for testing for the HLA-B27 antigen comprising a mixture containing a first antibody capable of binding and blocking the HLA-B7 antigen and a second antibody capable of binding to the HLA-B27 antigen and wherein said second antibody is labelled so as to be detectable.

5. A composition as claimed in claim 4, wherein said second antibody is radio-labelled.

6. A composition as claimed in claim 4, wherein said second antibody is labelled with an enzyme to react with a substrate to produce a detectable change.

* * * * *